United States Patent
Peterson et al.

(10) Patent No.: US 11,096,725 B2
(45) Date of Patent: Aug. 24, 2021

(54) REDUCTION SCREW TAB BREAK OFF AND STORAGE INSTRUMENT

(71) Applicant: Medos International Sarl, Le Locle (CH)

(72) Inventors: Joseph Peterson, South Dartmouth, MA (US); Frank Spratt, Middleboro, MA (US)

(73) Assignee: Medos International Sarl, Le Locle (CH)

( * ) Notice: Subject to any disclaimer, the term of this patent is extended or adjusted under 35 U.S.C. 154(b) by 169 days.

(21) Appl. No.: 16/276,324

(22) Filed: Feb. 14, 2019

(65) Prior Publication Data

US 2020/0261124 A1    Aug. 20, 2020

(51) Int. Cl.
*A61B 17/70* (2006.01)
*A61B 90/00* (2016.01)

(52) U.S. Cl.
CPC ...... *A61B 17/7085* (2013.01); *A61B 17/7032* (2013.01); *A61B 17/7086* (2013.01); *A61B 17/7091* (2013.01); *A61B 90/03* (2016.02); *A61B 17/7035* (2013.01); *A61B 2090/037* (2016.02)

(58) Field of Classification Search
CPC . A61B 17/7085; A61B 90/03; A61B 17/7032; A61B 17/7086; A61B 17/7091; A61B 2090/037; A61B 17/7035; A61B 17/8863; A61B 17/70774–7092
See application file for complete search history.

(56) References Cited

U.S. PATENT DOCUMENTS

| | | | |
|---|---|---|---|
| 5,573,530 A * | 11/1996 | Fleury | A61B 17/221 606/1 |
| 9,510,875 B2 | 12/2016 | Reitblat et al. | |
| 9,743,958 B2 | 8/2017 | Ishii et al. | |
| 2007/0213716 A1* | 9/2007 | Lenke | A61B 17/7077 606/264 |
| 2012/0109208 A1 | 5/2012 | Justis et al. | |
| 2014/0277195 A1* | 9/2014 | McBride | A61B 17/3421 606/86 A |
| 2016/0128847 A1* | 5/2016 | Kurtaliaj | A61B 17/88 623/17.16 |
| 2016/0302838 A1* | 10/2016 | Cormier | A61B 17/7074 |
| 2016/0346017 A1 | 12/2016 | Meyer et al. | |
| 2017/0215928 A1 | 8/2017 | Ishii et al. | |
| 2018/0263675 A1* | 9/2018 | Erramilli | A61B 17/8863 |

\* cited by examiner

*Primary Examiner* — Nicholas J Plionis
(74) *Attorney, Agent, or Firm* — Mintz Levin Cohn Ferris Glovsky and Popeo, P.C.

(57) ABSTRACT

Various exemplary methods and devices are provided for the removal and retention of bone screw rod reduction tabs extending from one or more bone screws implanted in a spinal column during a surgical procedure. In one embodiment, a removal and retention tool is provided having an elongated shaft with a channel formed therein that is configured to receive a rod reduction tab. The elongate shaft can be advanced over a rod reduction tab on a screw, and moved laterally to detach the reduction tab from the screw. The tool can include features to engage and retain the detached tab within the channel. Moreover, the tool can be configured to receive and retain multiple tabs, thus eliminating the need to remove the tool from a surgical site. The tool can also include a release actuator for releasing any tabs stored within the elongate shaft as may be needed.

18 Claims, 8 Drawing Sheets

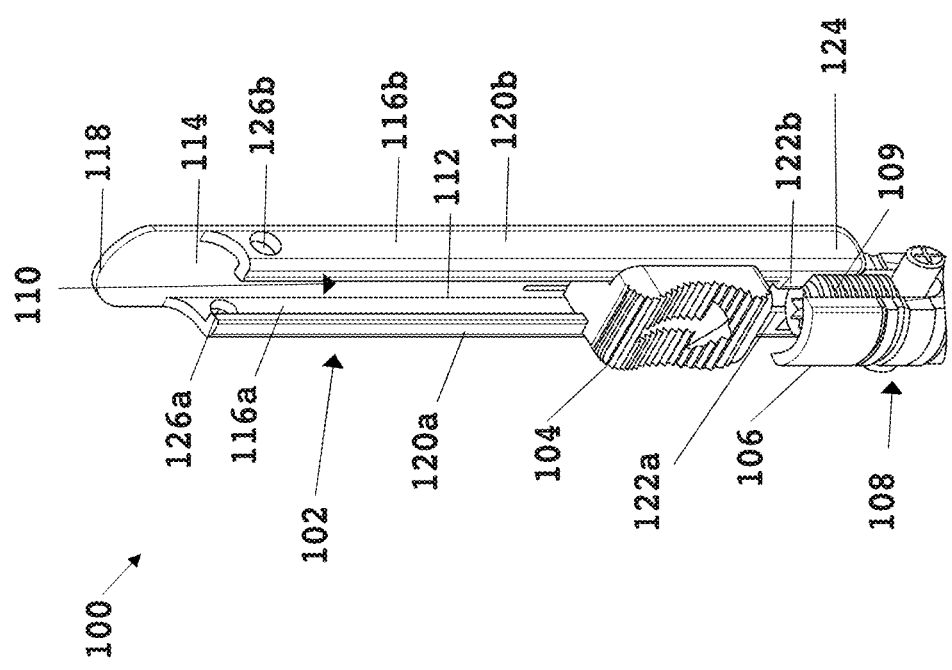

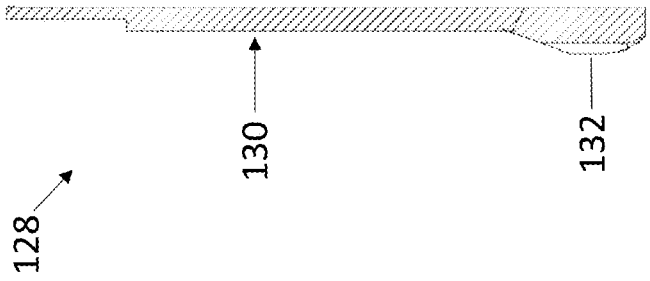
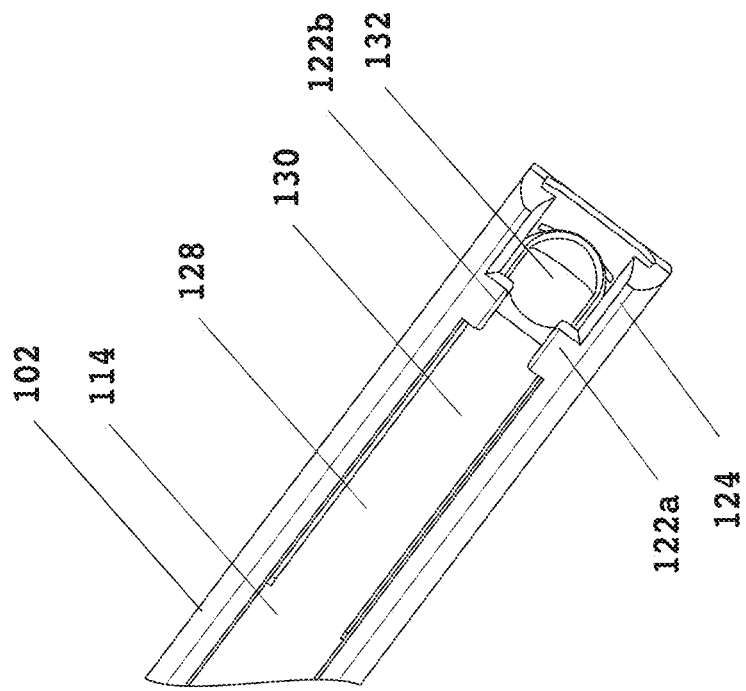

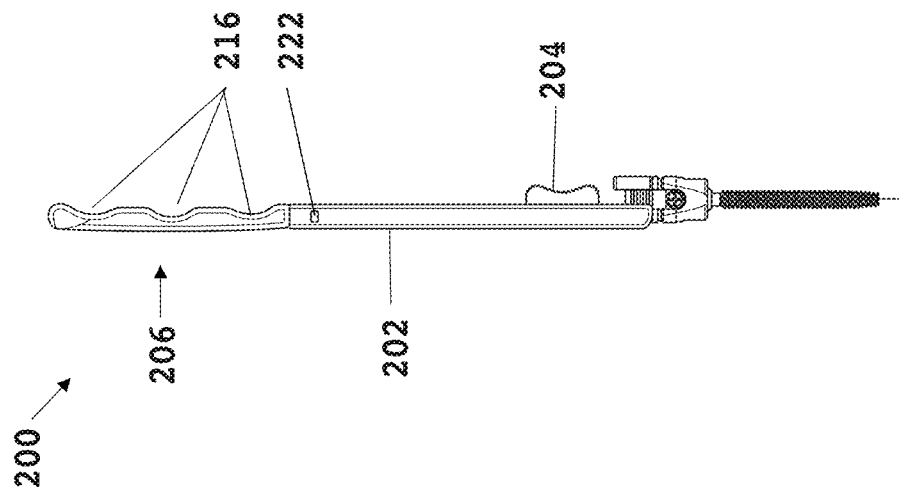
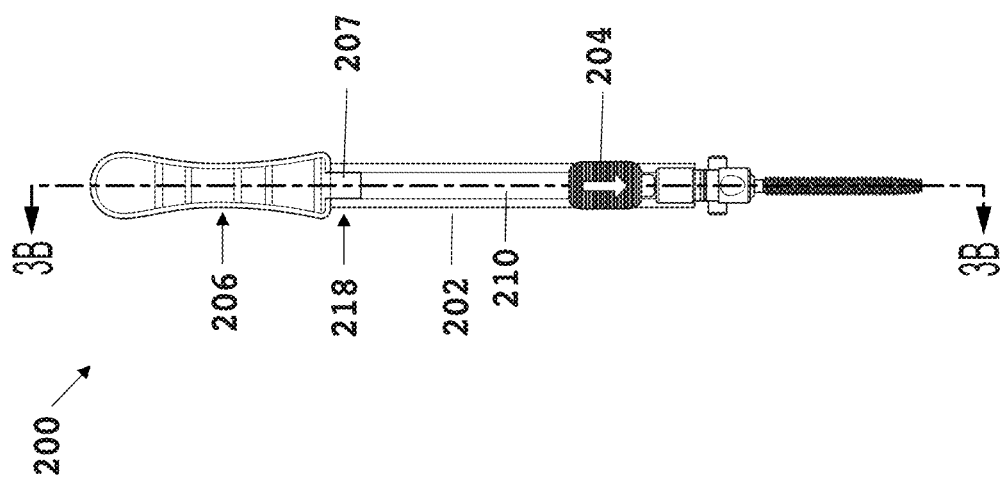

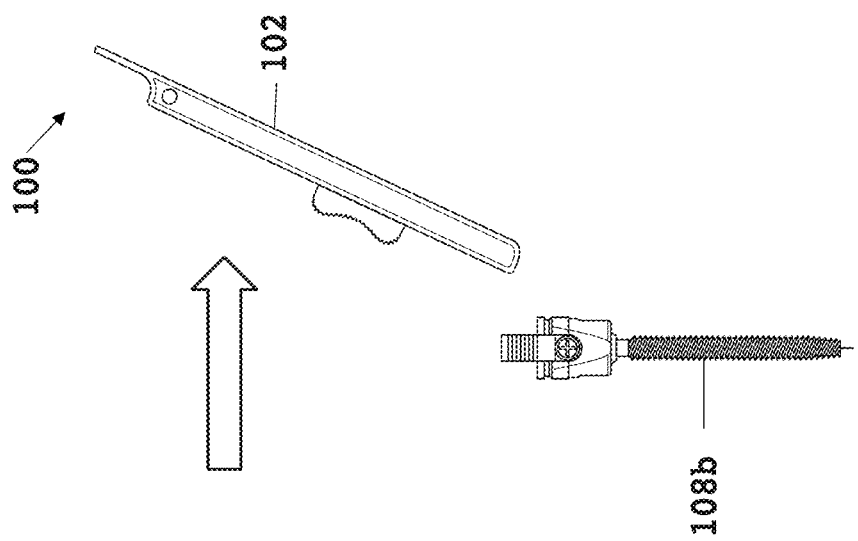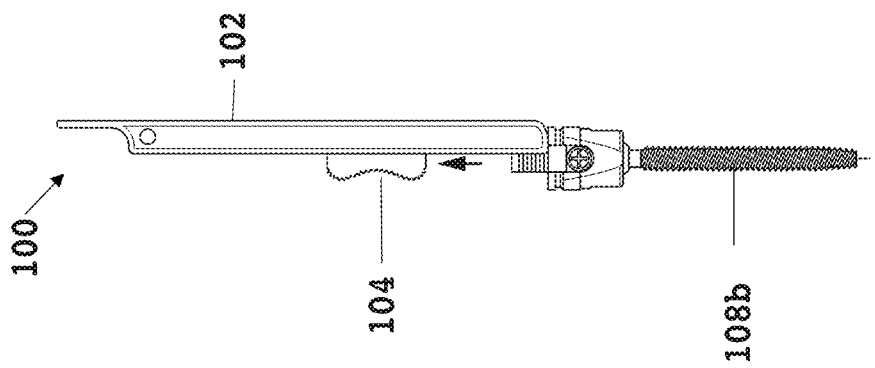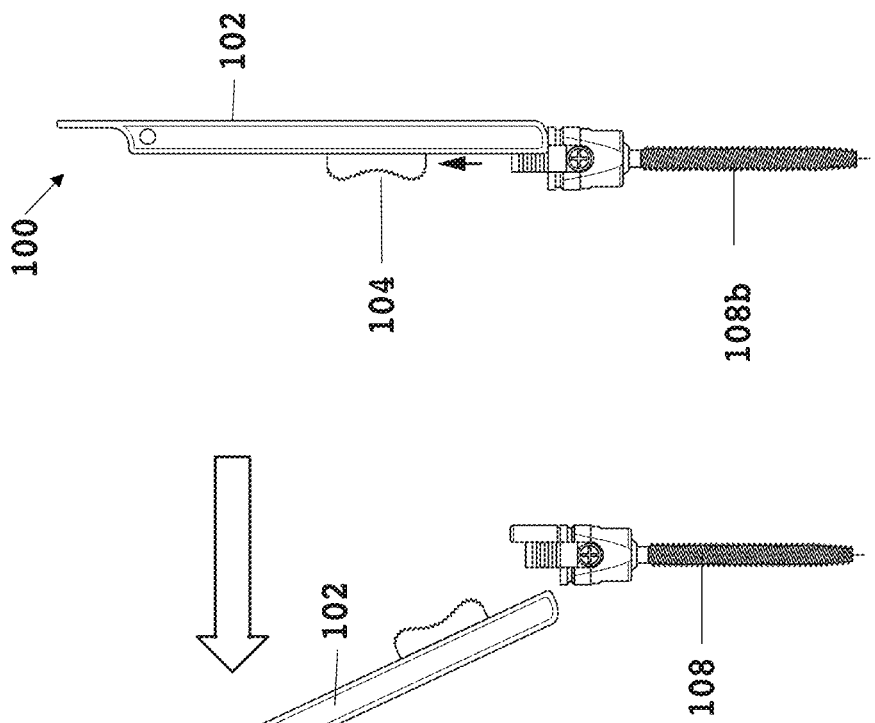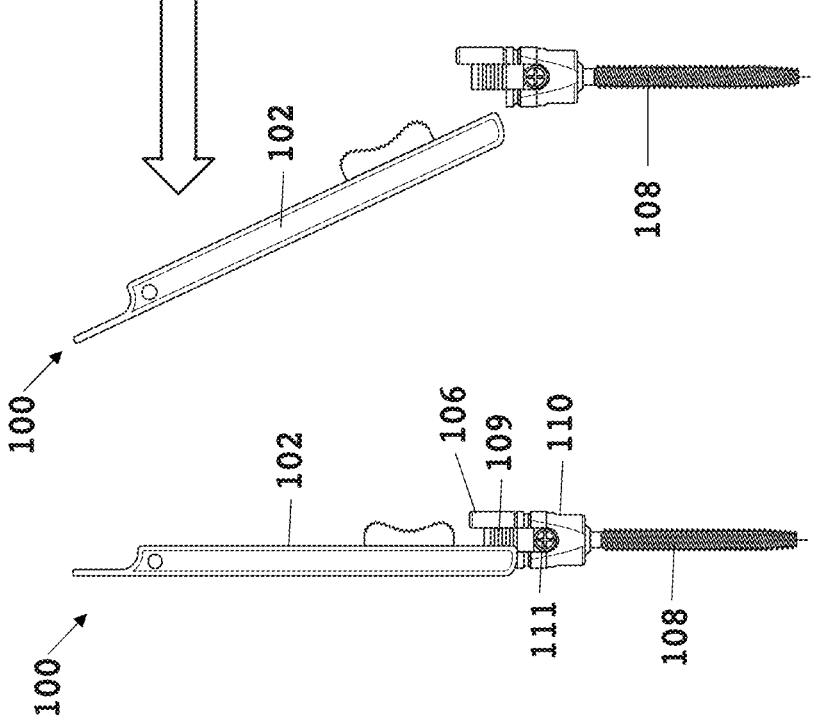

REDUCTION SCREW TAB BREAK OFF AND STORAGE INSTRUMENT

FIELD

Surgical devices, systems, and methods are provided for the removal and retention of bone screw rod reduction tabs.

BACKGROUND

Some spinal surgeries allow the use of polyaxial or monoaxial screws that feature integral rod reduction tabs. The reduction tabs can be used intraoperatively to facilitate reduction of a spinal rod into the receiver head of the anchor, and can be subsequently broken off in-situ and then disposed of. The reduction tabs have radial grooves scored on the inner and outer surfaces thereof where the tabs are intended to break off. The break off maneuver is initiated by applying a lateral load to the tab until it fractures at the score line. This has to be done independently to each reduction tab. The load required to fracture a tab is greater than what can typically be imposed by hand. Furthermore, once the break off is accomplished, the tab fragment must be controlled/retained in-situ so that it can be safely removed from the incision site. Therefore, an instrument is required to safely accomplish the break off task and to retain the broken-off tabs for safe removal from the body.

Accordingly, there remains a need for systems, methods and devices for the removal and retention of bone screw rod reduction tabs.

SUMMARY

Surgical devices, systems, and methods are provided for the removal and retention of bone screw rod reduction tabs. The devices, systems, and methods described herein can remove and retain multiple bone screw rod reduction tabs placed in the body without requiring removal of the tool from the body. Moreover, the devices, systems, and methods employ a simpler, smaller geometry than that used in currently existing tab removal devices and are lighter in weight and utilize a reduced number of parts, allowing for improved cleaning and sterilization of the device. Several tabs can be removed from one or more bone screws without the need to remove the device and the detached tab from the patient's body. By reducing the frequency of tool removal from the body, a user can correspondingly reduce the risk of contamination and reduce the length of a procedure.

In one embodiment, a tool for breaking off and retaining a rod reduction tab on a spinal screw is provided. The tool can include an elongate shaft having rails extending along opposed sides thereof between proximal and distal ends thereof. The rails can define a channel therebetween which can be configured to slidably receive at least one rod reduction tab on a spinal screw. In other embodiments, the channel can be configured to receive and store at least four rod reduction tabs. The elongate shaft can further include a deflectable retaining member disposed within the channel that can be configured to frictionally engage a rod reduction tab received within the channel. In some embodiments, the deflectable retaining member can include a projection on a distal end thereof that protrudes into the channel. The elongate shaft can include at least one stop adjacent the distal end that can be configured to retain a release actuator slidably disposed within the channel. In one aspect, the at least one stop can be in the form of a retaining bar extending across the channel.

In some embodiments, the release actuator can be configured to slide proximally in response to receipt of a rod reduction tab within the channel. The release actuator can also be configured to advance distally to overcome a bias applied by the deflectable retaining member and it can be configured to distally eject any rod reduction tabs disposed within the channel. In some embodiments, the release actuator can include a thumb concavity configured to seat a user's thumb. In other embodiments, the release actuator can include a distal extension configured to abut against a proximal end of a rod reduction tab disposed within the channel. In yet other embodiments, the distal extension can be configured to deflect the deflectable retaining member out of the channel. In other embodiments, the tool can include a handle coupled to the proximal end to the shaft.

In another embodiment, a system for implanting a spinal implant is provided. The system can include a spinal screw having a proximal rod receiving head and an elongate shank extending distally therefrom. The rod receiving head can include first and second break-off rod reduction tabs extending proximally therefrom. The system can further include a removal and retention tool having an elongate shaft with a channel extending therethrough. The channel can be sized to receive the first rod reduction tab, and the removal and retention tool can be configured to pivot laterally relative to the receiver head to break the first rod reduction tab off of the receiver head. A deflectable tang within the channel can be configured to retain the first rod reduction tab within the channel. The channel can also be sized to receive the second rod reduction tab. When the second rod reduction tab is received within the channel, the first rod reduction tab can slide proximally within the channel. The removal and retention tool can be configured to pivot laterally relative to the receiver head to break the second rod reduction tab off of the receiver head. The deflectable tang can retain the second rod reduction tab within the channel.

In other embodiments, the system can further include a set screw threadably matable with the proximal rod receiving head. The set screw can be threaded into the proximal rod receiving head. The removal and retention tool can include at least one stop extending across the channel.

In other embodiments, the system can include a handle coupled to the proximal end of the elongate shaft. In some embodiments, the system can include at least one stop on the elongate shaft adjacent the distal end. The at least one stop can be configured to retain a release actuator slidably disposed within the channel. In yet other embodiments, the channel can be configured to receive and store at least four rod reduction tabs.

In some embodiments, the release actuator can include a thumb concavity configured to seat a user's thumb. In other embodiments, the release actuator can include a distal extension configured to abut against a proximal end of the first and second rod reduction tabs when one of the first and second rod reduction tabs is disposed within the channel. In some embodiments, the deflectable tang can include a distal end with a protrusion formed thereon and protruding into the shaft channel. The protrusion can be configured to frictionally engage and retain the rod reduction tabs within the channel.

In another embodiment, a method for breaking off a plurality of rod reduction tabs from at least one spinal screw is described. The method can include advancing a distal end of a removal and retention tool over a first rod reduction tab on a spinal screw implanted in vertebra such that the first rod reduction tab is disposed within a channel extending along an elongate shaft of the tool. As the first rod reduction tab is advanced past the deflectable tab, the deflectable tab in the channel can deflect outward. The method can further include moving the tool laterally to cause the first rod reduction tab to break away from the spinal screw. The deflectable tab can frictionally engage the first rod reduction tab to retain the first rod reduction tab within the channel. In some embodiments, the distal end of the removal and retention tool can abut a surface of a set screw disposed within the spinal screw to limit the distal advancement of the removal and retention tool over the first rod reduction tab.

In other embodiments, the method can include advancing the distal end of the removal and retention tool over a second rod reduction tab on the spinal screw. As the second rod reduction tab is received into the distal end of the removal and retention tool, the first rod reduction tab can move proximally within the channel. The method can further include moving the tool laterally to cause the second rod reduction tab to break away from the spinal screw. The deflectable tab can frictionally engage the second rod reduction tab to retain the second rod reduction tab within the channel.

In other embodiments, the method can include repeating the advancing and moving steps with at least one additional rod reduction tab on at least one additional spinal screw such that at least three rod reduction tabs are retained within the channel. In other embodiments, the method can further comprise distally advancing a release actuator slidably disposed within the channel to advance a first rod reduction tab past the deflectable tab and can thereby eject the first rod reduction tab from the removal and retention tool.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 1A is a perspective view of one exemplary embodiment of a bone screw rod reduction tab removal device having an elongate shaft and a release actuator;

FIG. 1B is a perspective view of a distal portion of the elongate shaft of FIG. 1A;

FIG. 1C is a side view of a retaining member of the elongate shaft of FIG. 1B;

FIG. 2A is a front view of another embodiment of a rod reduction tab removal tool having an elongate shaft, a release actuator, and a handle, showing the device coupled to a bone screw;

FIG. 2B is a side view of the removal tool of FIG. 2A;

FIG. 4A is a side view of the rod reduction tab removal tool of FIG. 1A, shown advanced over a first rod reduction tab coupled to a bone screw;

FIG. 4B is a side view of the rod reduction tab removal tool of FIG. 4A after a lateral force has been applied to remove and retain the first rod reduction tab from the bone screw;

FIG. 4C is a side view of the rod reduction tab removal tool of FIG. 4B advanced over a second rod reduction tab coupled to the bone screw; and FIG. 4D is a side view of the rod reduction tab removal tool of FIG. 4C after a lateral force has been applied to remove and retain the second rod reduction tab from the bone screw.

DETAILED DESCRIPTION

Figure 1E:
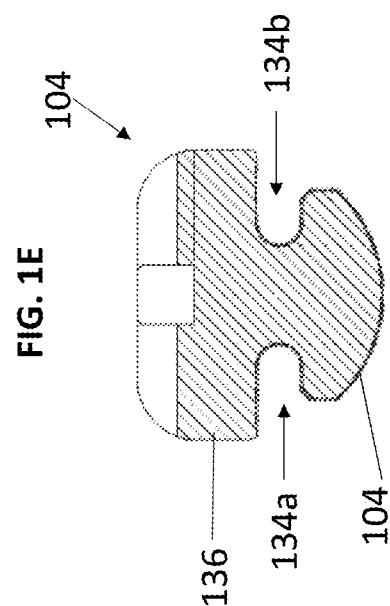
FIG. 1E is a cross-sectional view of the release actuator of FIG. 1D.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for the removal and retention of bone screw rod reduction tabs. In general, a removal and retention tool is provided having an elongated shaft with a channel formed therein that is configured to receive a rod reduction tab. The elongate shaft can be advanced over a rod reduction tab on a screw, and moved laterally to detach the reduction tab from the screw. The tool can include features to engage and retain the detached tab within the channel. Moreover, the tool can be configured to receive and retain multiple tabs, thus eliminating the need to remove the tool from a surgical site. The tool can also include a release actuator for releasing any tabs stored within the elongate shaft as may be needed. The tools disclosed herein employ a simpler, smaller geometry than that used in currently existing tab removal tools, and as such can be relatively lighter in weight. The tools can also have a reduced number of parts, which allows for improved cleaning and sterilization of the tool.

FIGS. 1A-1E show one exemplary embodiment of a rod reduction tab removal and retention tool 100. As shown, the tool has an elongate shaft 102 with a channel 110 extending longitudinally therethrough. The channel 110 is configured to receive, remove, and store at least one rod reduction tab 106 on a bone screw 108 implanted in bone during a surgical procedure. The channel 110 can include a retaining feature that is configured to retain the reduction tab(s) 106 within the channel, and a release actuator 104 that is slidably disposed within the channel 110 and that can be configured to eject any rod reduction tabs 106 stored within the channel 110.

The elongate shaft 102 can have a variety of shapes and sizes, but in the illustrated embodiment it has a substantially rectangular cross-sectional shape with a hollow center portion that forms the channel 110. In particular, the shaft can have a back wall 114 and two rails 116a, 116b extending along opposed sides thereof. Each rail 116a, 116b can include an outer sidewall extending substantially perpendicular to the back wall 114, and an inwardly extending lip 120a, 120b along the front edge of each sidewall that defines an open front 112 of the channel 110. The open front 112 can be configured to slidably receive the release actuator 104, as will be discussed in more detail below.

The geometry of the channel 110 and the track defined by the rails 116a, 116b can vary based on the geometry of the rod reduction tabs to be retained within the channel, and thus other channel geometries are contemplated (e.g., oval, D-shaped, etc.). As will be explained in more detail with respect to FIG. 1E, in the illustrated embodiment the rails 116a, 116b form a channel that is substantially D-shaped, with a rounded profile along the back wall 114 of the elongate shaft 102 that conforms to the outer convex shape of the reduction tabs 106 on the bone screw 108.

As further shown in FIG. 1A, the elongate shaft 102 can also feature a rounded proximal end 118 extending proximally from the back wall 114 of the elongate shaft 102 to facilitate grasping of the tool 100, or to facilitate mating with a handle as will be discussed below with respect to other embodiments.

A length of the elongate shaft 102 extending between proximal end distal ends 118, 124 thereof can vary as needed, but in an exemplary embodiment the shaft 102 has a length that allows the distal end 124 to be positioned within a patient's body, while the proximal end 118 remains external to the body for grasping by a user. The length can also vary based on the desired number of rod reduction tabs to be retained therein. In certain exemplary embodiments, the elongate shaft 102 can had a length of at least about 40 mm for retaining 4 tabs, and more preferably has a length of about 90-100 mm such that it can be configured to store approximately 10 extension tabs. The length can vary depending on the length of each extension tab and the number of tabs to be held.

As indicated above, the tool 100 can also include a retaining feature for retaining one or more reduction tabs 106 within the channel 110. While the retaining feature can have a variety of configurations, in the illustrated embodiment the retaining feature is in the form of a deflectable retaining tab 128 formed in the back wall 114 of the elongate shaft 102. The illustrated deflectable retaining tab 128 is formed from a u-shaped cut-out in the back wall 114 of the elongate shaft 102, thus allowing the tab 128 to deflect. In other words, the tab 128 functions like a spring having a resting position aligned with the back wall 114 of the elongate shaft 102. In other embodiments, the retaining tab 128 can be formed separate from the shaft 102 and can be mated thereto, or other configurations are possible.

In order to aid in engagement of a rod reduction tab, the deflectable retaining tab 128 can include an engagement feature on a front side 130 thereof that faces and extends into the channel 110. The engagement feature can be in the form of a protrusion 132 disposed thereon and protruding into the channel 110, as shown in FIGS. 1B and 1C. When in a resting position, the protrusion 132 can be configured to block movement of any rod reduction tabs 106 positioned proximal thereof from moving distally within the channel 110, thereby preventing the tabs from falling out of the channel 110. However, when a force is applied to the protrusion 132, the retaining tab 128 can deflect radially outward away from the channel 110, allowing a tab 106 to pass. As will be discussed in more detail below, a force can be applied when the elongate shaft 102 is advanced over a rod reduction tab for removing the tab from a spinal screw, or when the release actuator 104 is moved distally to cause the distal-most tab to abut the protrusion 132. When the tab is fully seated in the channel 110, the protrusion 132 can function to frictionally engage the rod reduction tab to retain the tab within the channel 110 during removal. A person skilled in the art will appreciate that a variety of other techniques can be used to retain one or more rod reduction tabs within the channel 110.

Figure 1D:
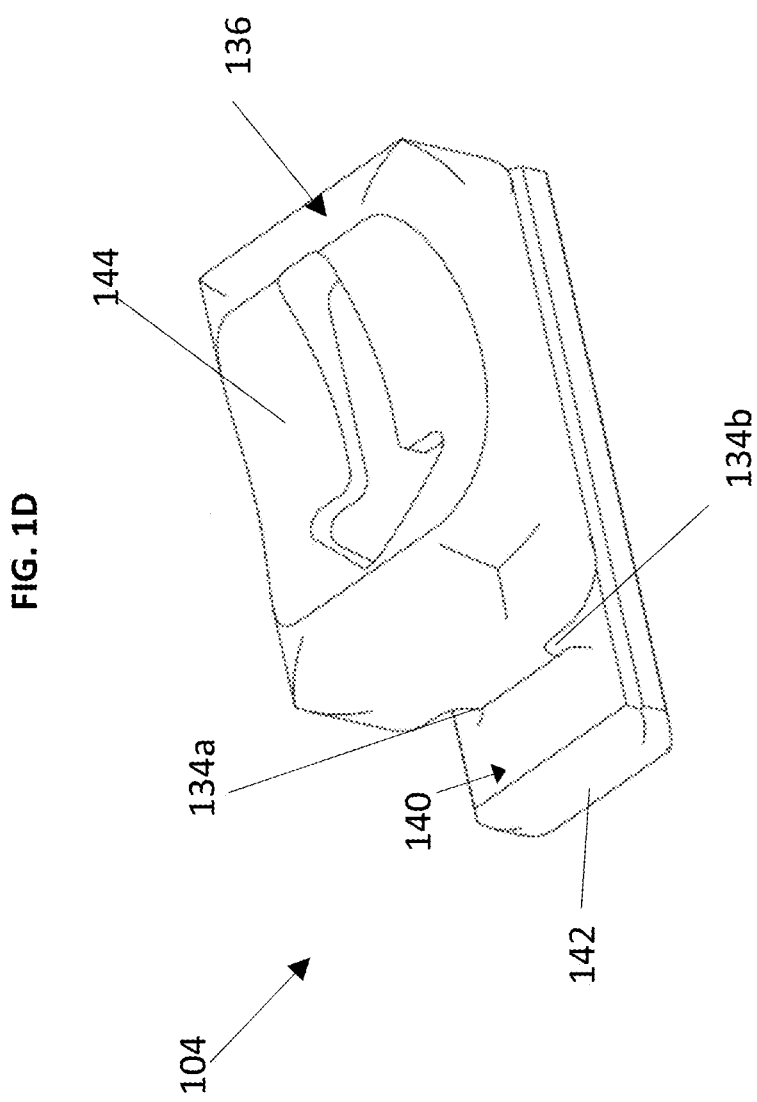
FIG. 1D is a perspective view of the release actuator of FIG. 1A.

As indicated above, the tool 100 can include a release actuator 104 that allows the rod reduction tabs disposed within the channel 110 to be selectively released therefrom. While the release actuator can have a variety of configurations, in the illustrated embodiment the release actuator 104 is in the form of a thumb button that is slidably disposed within the open front 112 between the rails 116a, 116b. As best shown in FIGS. 1D and 1E, the release actuator 104 has a sliding plate 140 that sits within the channel 110 and is engaged between the rails 116a, 116b, and a housing 136 coupled to a front of the sliding plate 140. The sliding plate 140 can have a shape that matches the shape of the channel 110, such as D-shaped as shown in FIG. 1E. The housing 136 sits outside of the rails 116a, 116b and it can have a concavity 144 formed therein for seating a user's thumb. The concavity 144 can have surface features, such a knurling or a roughened portion, to facilitate grasping. The housing 136 can have a variety of other configurations to allow a user to grasp and slide the release actuator 104. As further shown in FIGS. 1D and 1E, grooves 134a, 134b can be formed between the housing 136 and the sliding plate 140 for allowing the lip 120a, 120b on each rail 116a, 116b to slide between the housing 136 and the sliding plate 140.

Referring back to FIG. 1A, when the release actuator 104 is disposed within the channel 110, a portion of the sliding plate 140 that extends distally beyond a distal end of the housing 136 can form an extension tab 142 that contacts a proximal end of a rod reduction tab 106 seated within the channel 110. Since the release actuator 104 is freely slidable, the reduction tab 106 can cause the release actuator to move proximally within the channel 110. As subsequent rod reduction tabs are loaded into the channel 110, the release actuator 104 will continue to slide proximally within the channel 110. When a procedure is complete, a user can grasp the release actuator 104 by placing their thumb (or other finger) within the concavity 144 and they can advance the release actuator 104 distally within the channel. This will force all rod reduction tabs 106 in the channel 110 to move distally. As each reduction tab passes the protrusion 132 on the deflectable retaining member 128, the force applied to the reduction tabs 106 by the release actuator 104 will cause the deflectable retaining member 128 to deflect radially outward, away from the channel 110. The rod reduction tabs can thus move distally past the protrusion 132 and out of the channel to be ejected from the tool 100.

In order to retain the release actuator 104 within the channel 110, each of the rails 116a, 116b can include a stop feature formed adjacent a distal end 124 of the elongate shaft 102. As best shown in FIG. 1B, each rail 116a, 166b has a rectangular stop 122a, 122b feature formed thereon and extending toward one another across the open front 112. The stops 122a, 122b will limit distal movement of the release actuator 104, preventing the release actuator 104 from sliding out of the distal end 124 of the elongate shaft 102.

The tool 100 shown in FIGS. 1A-1E can be manufactured and assembled using a variety of techniques, including conventional machining techniques or using additive manufacturing techniques for making a 3D printed tool. In an exemplary embodiment, the shaft 102 and the release actuator 104 are separately manufactured as monolithic components using 3D printing techniques, and then assembled to form the tool. In particular, the tool 100 can be formed from two components, namely the elongate shaft 102 and the release actuator 104, and the two components can be assembled by inserting the release actuator 104 into the proximal end of the elongate shaft 102. In order to retain the release actuator 104 within the channel 110 in the elongate shaft 102, a pin (not shown) can be inserted through opposed holes 126a, 126b (shown in FIG. 1A) formed in a proximal end of the elongate shaft 102. Other retaining mechanisms can be used, as will be appreciated by a person having ordinary skill in the art.

The tool 100 of FIGS. 1A-1E can have a variety of other configurations, and in other embodiments the tool can include a handle to further facilitate grasping and manipulation of the tool. FIGS. 2A-2B illustrate another embodiment of a rod reduction tab removal and retention tool 200 having a handle 206 coupled to a proximal end 218 of the elongate shaft 202. The elongate shaft 202 and release actuator 204 can be functionally the same as the elongate shaft 102 and the release actuator 104 of the FIGS. 1A-1E, and thus the description below relates only to the differences between tool 100 and tool 200. As shown, the handle 206 extends proximally from and is coupled to the proximal end 218 of the elongate shaft 202. The illustrated handle 206 has a generally elongate configuration and includes multiple depressions 216 formed therein to facilitate grasping thereof. The handle 206 can, however, have a variety of other configurations. In order to facilitate mating of the handle 206 to the elongate shaft 202, the handle 206 can include a distal protrusion or extension 207 that extends into the channel 210 extending through the elongate shaft 202. The distal extension 207 can include tabs (not shown) projecting from opposed sides thereof and configured to form a snap-fit engagement with opposed holes (one hole 222 is shown in FIG. 2B) formed in the proximal end of the elongate shaft 206. Alternatively, the extension can include a thru-bore and a pin can be placed through the holes 222 and the through bore to couple the handle 206 to the elongate shaft 202. A person skilled in the art will appreciate that a variety of mating techniques can be used to mate the handle 206 to the shaft 202. Once mated to the shaft 202, the handle 206 will function to retain the release actuator 204 within the channel 210.

As with the embodiment of FIGS. 1A-1B, the components of tool 200 can be manufactured using conventional machining techniques or using additive manufacturing techniques for making a 3D printed tool. In an exemplary embodiment, the handle 206, shaft 202, and release actuator 204 are each formed as separate, monolithic components using 3D printing techniques, and then assembled to form the tool 200. The tool 200 can be assembled by inserting the release actuator 204 into the channel 210 at the proximal end 218 of the elongate shaft 202, and then inserting the extension 207 on the handle 206 into the channel to mate the handle 206 to the shaft 202. Once the handle 206 is attached to the shaft 202, the release actuator 204 is retained within the channel 210.

In other embodiments, a handle can be overmolded around a post formed on a proximal end of the tool. FIGS. 3A-3D illustrate an embodiment of a rod reduction tab removal and retention tool 300 having a post 306 integrally formed with and extending proximally from the proximal end 318 of the elongate shaft 302. The remainder of the tool 300, including the elongate shaft 302 and release actuator 304, are functionally the same as the elongate shaft 102 and the release actuator 104 of FIGS. 1A-1E, with any differences discussed in detail below.

Figure 3A:
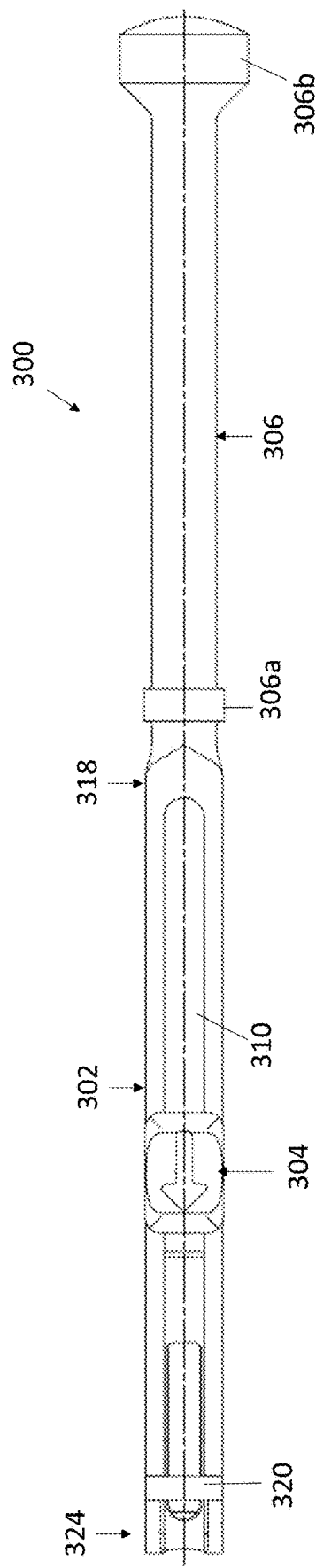
FIG. 3A is a front view of another embodiment of a rod reduction tab removal tool having an elongate shaft, a release actuator, and a proximal post for supporting a handle.
Figure 3B:
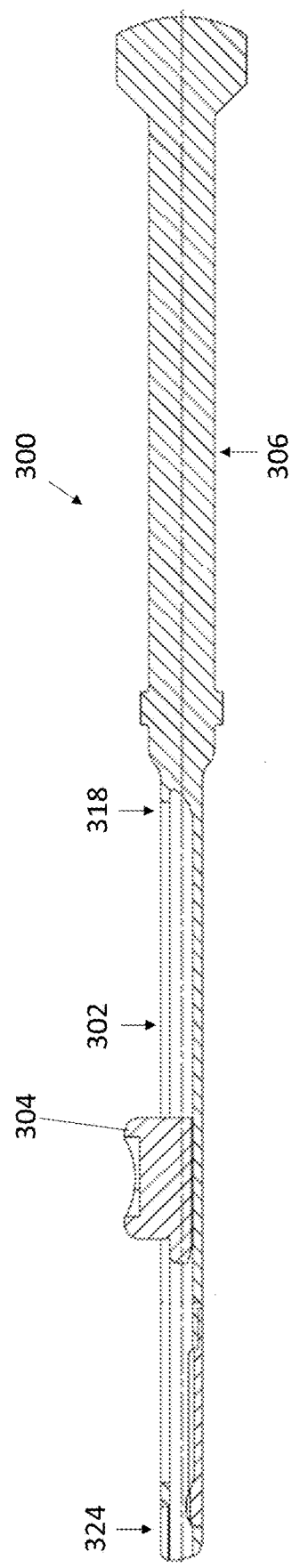
FIG. 3B is a cross-sectional side view of the removal tool of FIG. 3A, taken about the longitudinal center line of the tool.
Figure 3C:
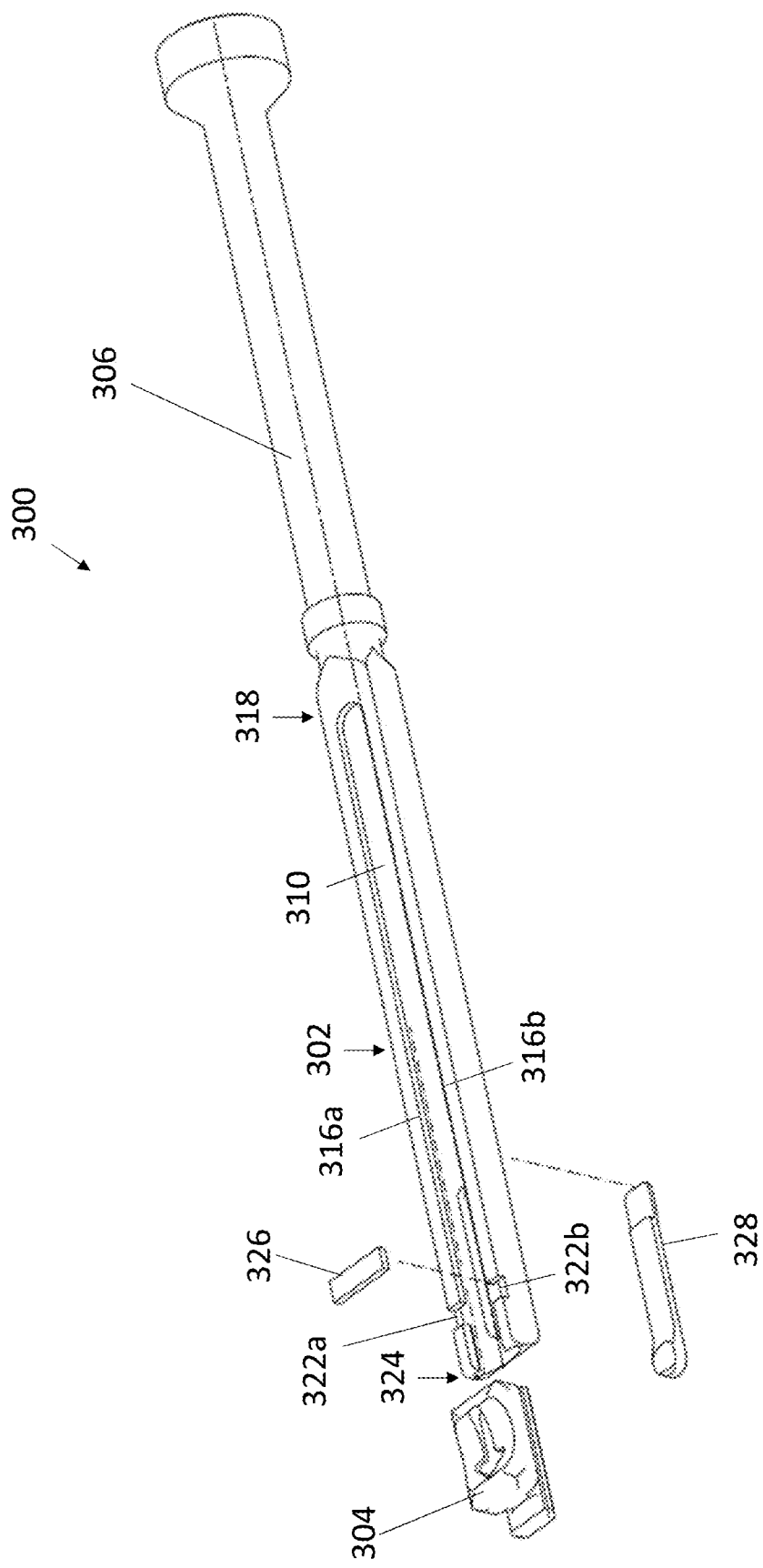
FIG. 3C is an exploded view of the removal tool of FIG. 3A.
Figure 3D:
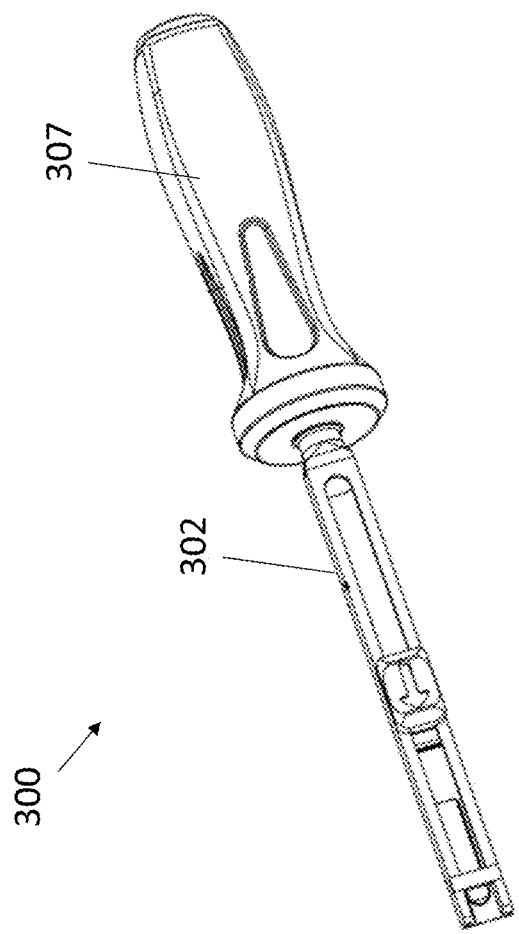
FIG. 3D is a perspective view of the removal tool of FIG. 3A, showing a handle overmolded onto the post.

As shown, the post 306 can be integrally formed with the elongate shaft 302. While the post 306 can have a variety of configurations depending on the desired configuration of the handle, in the illustrated embodiment the post 306 is generally cylindrical with a distal flange 306a and a proximal flange 306b. The flanges 306a, 306b can aid in allowing a handle to be molded around the post 306 and fixedly attached thereto. FIG. 3D illustrates a plastic handle 307 molded over the post 306 and having a cylindrical shape to facilitate grasping. Other handle shapes are contemplated, including T-shaped.

Since distal end of the post 306 is integrally formed with the elongate shaft 302, the proximal end 318 of the elongate shaft 302 is closed. As a result, the channel 310 extending through the elongate shaft 302 is likewise closed at the proximal end 318. Thus, in order to assemble the tool 300, the release actuator 304 can be inserted into the distal end 324 of the elongate shaft 302, as shown in FIG. 3C. Once seated in the channel 310, the release actuator 304 can be retained therein using a variety of techniques. In the illustrated embodiment, the shaft 302 includes a stop feature in the form of a stop bar 326 that is seated within cut-outs 322a, 322b formed in each rail 316a, 316b. The stop bar 326 can be welded or otherwise permanently affixed to the rails 316a, 316b to retain the release actuator 304 channel 310. As further shown in FIG. 3C, in this embodiment the deflectable retaining member 328 can be formed as a separate component and can be welded onto the elongate shaft 102. Such a configuration allows the separate components to be manufactured using various manufacturing techniques, such as conventional machining techniques or using additive manufacturing techniques for making a 3D printed tool. In an exemplary embodiment, the tool of FIGS. 3A-3D is machined from bar stock, and the handle is overmolded over the tool and the components assembled as shown in FIG. 3C.

FIGS. 4A-4D illustrate one exemplary method for removing and retaining a rod reduction tab from a bone screw using a rod reduction tab removal and retention tool. While the method is discussed in connection with tool 100, the method can be performed using any of the tools disclosed herein.

As shown, a bone screw 108 is implanted in bone (not shown) and a rod 111 is reduced into a receiver head 110 of the bone screw 108. A set screw 109 is applied to the screw 108 to retain the rod 111 within the receiver head 110. The illustrated set screw 109 has a distal portion with an outer diameter that is greater than an outer diameter of the proximal portion. As a result of this configuration, the set screw 109 can aid in positioning the elongate shaft 102 relative to the reduction tab 106, as discussed below.

With the rod 111 secured to the spinal screw 108, the tool 100 can be manipulated to advance the elongate shaft 102 over the rod reduction tab 106 such that the tab extends into the channel. As the tab 106 reaches the protrusion 132 on the deflectable retaining member 128, the force applied to advance the shaft 102 over the tab 106 will cause the deflectable retaining member 128 to deflect radially outward and away from the channel. The protrusion 132 will thus frictionally engage the tab 106. The distal end of the shaft 102 will abut against an upper surface of the distal, larger diameter portion of the inner set screw 109, as shown in FIG. 1A.

Once the tool is fully advanced over the tab 106, lateral movement of the proximal end of the shaft 102 will cause the shaft 102 to pivot relative to the bone screw 108, as shown in FIG. 4B, thereby causing the reduction tab disposed within the channel of the shaft to pivot relative to the bone screw 108. A predefined breaking point can be defined between the tab 106 and the receiver head 110, thus allowing the tab 106 to break apart from the bone screw 108. The deflectable retaining member 128 will retain the broken-off extension tab 106 within the channel 110.

The tool can then be relocated to a second bone screw 108b, as shown in FIG. 4C, and the process can be repeated to remove a second bone screw rod reduction tab, as shown in FIG. 4D. As the shaft 102 is advanced over the second reduction tab, the second tab will cause the first tab to move proximally within the channel. Proximal movement of the first tab will in turn cause the release actuator 104 to move proximally, as shown in FIG. 4C. Moreover, the first tab will be moved proximal of the retaining member 128, allowing the retaining member 128 to frictionally engage the second tab.

The process can be repeated until the channel 110 is completely filled with broken-off bone screw rod reduction tabs 106. The position of the release actuator 104 at the proximal end of the shaft will indicate to a user that the channel is full. When the user is finished with the removal of bone screw rod reduction tabs, the tool can be removed from the body, and the user can slide the release actuator 104 distally to eject the reduction tab from the channel. As the tabs 106 are advanced distally, the deflectable retaining member 128 will deflected out of the channel 110 to permit the tabs to pass through the distal end of the elongate shaft 102.

The tools disclosed herein can be designed to be disposed of after a single use, or they can be designed to be used multiple times. In either case, however, the tool can be reconditioned for reuse after at least one use. Reconditioning can include any combination of the steps of disassembly of the tool, followed by cleaning or replacement of particular pieces, and subsequent reassembly. In particular, the tool can be disassembled, and any number of the particular pieces or parts of the tool can be selectively replaced or removed in any combination. Upon cleaning and/or replacement of particular parts, the tool can be reassembled for subsequent use either at a reconditioning facility, or by a surgical team immediately prior to a surgical procedure. Those skilled in the art will appreciate that reconditioning of a tool can utilize a variety of techniques for disassembly, cleaning/replacement, and reassembly. Use of such techniques, and the resulting reconditioned tool, are all within the scope of the present application.

Preferably, the tools and components described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the described devices and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A tool for breaking off and retaining a rod reduction tab on a spinal screw, the tool comprising:
    an elongate shaft having rails extending along opposed sides thereof between proximal and distal ends thereof and a back wall extending between the rails, wherein the back wall is disposed opposite an open side of the elongate shaft, the rails and the back wall defining a channel therebetween configured to slidably receive at least one rod reduction tab on a spinal screw, the elongate shaft further including a deflectable retaining member formed in the back wall and disposed within the channel and configured to frictionally engage a rod reduction tab received within the channel; and
    a release actuator slidably disposed within the channel, the release actuator being configured to slide proximally in response to receipt of a rod reduction tab within the channel, and the release actuator being configured to advance distally to overcome a bias applied by the deflectable retaining member and to distally eject any rod reduction tabs disposed within the channel.

2. The tool of claim 1, further comprising a handle coupled to the proximal end of the elongate shaft.

3. The tool of claim 1, further comprising at least one stop on the elongate shaft adjacent the distal end, the at least one stop being configured to retain the release actuator within the channel.

4. The tool of claim 3, wherein the at least one stop on the elongate shaft comprises a retaining bar extending across the channel.

5. The tool of claim 1, wherein the channel is configured to receive and store at least four rod reduction tabs.

6. The tool of claim 1, wherein the release actuator includes a thumb concavity configured to seat a user's thumb.

7. The tool of claim 1, wherein the release actuator includes a distal extension configured to abut against a proximal end of a rod reduction tab disposed within the channel.

8. The tool of claim 7, wherein the distal extension is configured to deflect the deflectable retaining member out of the channel.

9. The tool of claim 1, wherein the deflectable retaining member includes a projection on a distal end thereof protruding into the channel.

10. A tool for breaking off and retaining a rod reduction tab on a spinal screw, the tool comprising:
    an elongate shaft having an open distal end and a channel extending proximally from the open distal end to an opposite proximal end, the channel defined by rails extending along opposed sides thereof and a back wall extending between the rails, wherein the back wall is disposed opposite an open side of the elongate shaft, the channel configured to slidably receive at least one rod reduction tab on a spinal screw inserted into the open distal end, the elongate shaft further including a deflectable retaining member coupled to the back wall and disposed within the channel and configured to frictionally engage a rod reduction tab received within the channel; and a release actuator slidably disposed within the channel, the release actuator being configured to slide proximally along the rails in response to receipt of a rod reduction tab within the channel, and the release actuator being configured to advance distally along the rails to overcome a bias applied by the deflectable retaining member and to distally eject any rod reduction tabs disposed within the channel.

11. The tool of claim 10, further comprising a handle coupled to the proximal end of the elongate shaft.

12. The tool of claim 10, further comprising at least one stop on the elongate shaft adjacent the open distal end, the at least one stop being configured to retain the release actuator within the channel.

13. The tool of claim 12, wherein the at least one stop on the elongate shaft comprises a retaining bar extending across the channel.

14. The tool of claim 10, wherein the channel is configured to receive and store at least four rod reduction tabs.

15. The tool of claim 10, wherein the release actuator includes a thumb concavity configured to seat a user's thumb.

16. The tool of claim 10, wherein the release actuator includes a distal extension configured to abut against a proximal end of a rod reduction tab disposed within the channel.

17. The tool of claim 16, wherein the distal extension is configured to deflect the deflectable retaining member out of the channel.

18. The tool of claim 10, wherein the deflectable retaining member includes a projection on a distal end thereof protruding into the channel.

* * * * *